US008428322B2

(12) United States Patent
Wong et al.

(10) Patent No.: US 8,428,322 B2
(45) Date of Patent: Apr. 23, 2013

(54) METHOD AND SYSTEM FOR DETERMINING THE POSITION OF AN OPTIC CUP BOUNDARY

(75) Inventors: Wing Kee Damon Wong, Singapore (SG); Jiang Liu, Singapore (SG); Joo Hwee Lim, Singapore (SG); Huiqi Li, Singapore (SG); Ngan Meng Tan, Singapore (SG); Tien Yin Wong, Singapore (SG)

(73) Assignees: Singapore Health Services Pte Ltd, Singapore (SG); Agency for Science, Technology and Research, Singapore (SG); National University of Singapore, Singapore (SG)

( * ) Notice: Subject to any disclaimer, the term of this patent is extended or adjusted under 35 U.S.C. 154(b) by 94 days.

(21) Appl. No.: 13/140,011

(22) PCT Filed: Dec. 15, 2008

(86) PCT No.: PCT/SG2008/000482
§ 371 (c)(1),
(2), (4) Date: Jun. 15, 2011

(87) PCT Pub. No.: WO2010/071597
PCT Pub. Date: Jun. 24, 2010

(65) Prior Publication Data
US 2011/0243410 A1    Oct. 6, 2011

(51) Int. Cl.
*G06K 9/00* (2006.01)
(52) U.S. Cl.
USPC .......................................................... 382/128
(58) Field of Classification Search ........................ None
See application file for complete search history.

(56) References Cited

U.S. PATENT DOCUMENTS

| 6,030,079 A | 2/2000 | Torii |
| 6,053,865 A | 4/2000 | Sugiyama et al. |
| 2007/0109499 A1 | 5/2007 | Yan et al. |

FOREIGN PATENT DOCUMENTS

WO    WO 2009/139722    11/2009

OTHER PUBLICATIONS

World Health Organization, "Magnitude and Causes of Visual Impairment", Fact Sheet No. 282, 2 pgs., (Nov. 2004).
T.Y. Wong, et al., "The Epidemiology of Age Related Eye Diseases in Asia" , British Journal of Ophthalmology, vol. 90, No. 4, pp. 506-511, (Apr. 2006).
Paul J. Foster, et al., "The Prevalence of Glaucoma in Chinese Residents of Singapore: A Cross-Sectional Population Survey of the Tanjong Pagar District" , Epidemiology and Biostatistics, vol. 118, No. 8, pp. 1105-1111, (Aug. 2000).
H.A. Quigley, et al., "The Number of People with Glaucoma Worldwide in 2010 and 2020", British Journal of Ophthalmology, vol. 90, No. 3, pp. 262-267, (Mar. 2006).
Glaucoma Research Foundation, "Are you at Risk for Glaucoma?", retrieved on Jun. 28, 2011 from: http://www.glaucoma.org/glaucoma/are-you-at-risk-for-glaucoma.php, 2 pgs., (Jan. 13, 2011).

(Continued)

*Primary Examiner* — Stephen R Koziol
*Assistant Examiner* — Amandeep Saini
(74) *Attorney, Agent, or Firm* — Blakely, Sokoloff, Taylor & Zafman LLP (57) ABSTRACT

A method for determining the position of an optic cup boundary in a 2D retinal image. The method includes detecting kinks in blood vessels at an estimated boundary of the optic cup and the optic disc, and determining the position of the optic cup boundary in the 2D retinal image based on the detected kinks. The determined optic cup boundary may be used for determining a CDR which may in turn be used for determining a risk of contracting glaucomatous.

19 Claims, 7 Drawing Sheets

OTHER PUBLICATIONS

Anders Heijl, et al., "Reduction of Intraocular Pressure and Glaucoma Progression: Results From the Early Manifest Glaucoma Trial", Archives of Ophthalmology, vol. 120, No. 10, pp. 1268-1279, (Oct. 2002).

Naoto Inoue, et al., "Development of a Simple Diagnostic Method for the Glaucoma using Ocular Fundus Pictures", Proceedings of the 2005 IEEE, 27th Annual International Conference of the Engineering in Medicine and Biology Society, pp. 3355-3358, (Sep. 1-4, 2005).

Michael D. Abramoff, et al., "Automated Segmentation of the Optic Disc from Stereo Color Photographs using Physiologically Plausible Features,", Investigative Ophthalmology & Visual Science, vol. 48, No. 4, pp. 1665-1673, (Apr. 2007).

Juan Xu, et al., "Optic Disk Feature Extraction via Modified Deformable Model Technique for Glaucoma Analysis", Pattern Recognition, vol. 40, Issue 7, pp. 2063-2076, (Jul. 2007).

Jost B. Jonas, et al., "Ophthalmoscopic Evaluation of the Optic Nerve Head", Survey of Ophthalmology, vol. 43, No. 4, pp. 293-320, (Jan.-Feb. 1999).

Chunming Li, et al., "Level Set Evolution without Re-initialization: A New Variational Formulation ", Proceedings of the 2005 IEEE Computer Society Conference on Computer Vision and Pattern Recognition (CVPR '05), 7 pgs., (2005).

Huiqi Li, et al., "Image Based Diagnosis of Cortical Cataract", 30th Annual International IEEE EMBS Conference, pp. 3904-3907, (Aug. 20-24, 2008).

PCT International Search Report for PCT Counterpart Application No. PCT/SG2008/00482 containing Communication relating to the Results of the Partial International Search Report, 3 pgs., (Apr. 28, 2009).

PCT Written Opinion of the International Searching Authority for PCT Counterpart Application No. PCT/SG2008/000482, 4 pgs., (Apr. 28, 2009).

PCT International Preliminary Report on Patentability (Chapter II of the Patent Cooperation Treaty) for PCT Counterpart Application No. PCT/SG2008/000482, 9 pgs., (Apr. 6, 2010).

METHOD AND SYSTEM FOR DETERMINING THE POSITION OF AN OPTIC CUP BOUNDARY

CROSS-REFERENCE TO RELATED APPLICATION

This patent application is a U.S. National Phase application under 35 U.S.C. §371 of International Application No. PCT/SG2008/000482, filed Dec. 15, 2008, entitled A METHOD AND SYSTEM FOR DETERMINING THE POSITION OF AN OPTIC CUP BOUNDARY.

FIELD OF THE INVENTION

The present invention relates to a method and system for determining an optic cup boundary in a 2D retinal image. The method and system can be used to determine a CDR which may in turn be used for determining a risk of contracting glaucoma.

BACKGROUND OF THE INVENTION

Glaucoma is one of the leading causes of blindness worldwide. According to a World Health Organization report in 2004 [1], glaucoma is the second leading cause of blindness, with 12.3% of visual impairment globally being attributed to this disease. It has been estimated that more than half of the 70 million glaucoma cases are in Asia [2]. In Singapore, a recent community-based study [3] found that 3.2% of Chinese respondents over the age of 40 were found to have glaucoma. Furthermore, the disease is closely associated with age [4] and according to the Glaucoma Research Foundation [5], a person over the age of 60 is "six times more likely to get glaucoma". Given the rapidly aging population in many parts of the world, including Singapore, the prevalence of glaucoma is likely to increase.

Characterized by the death of ganglion nerve cells, glaucomatous damage is irreversible and permanent. Furthermore, noticeable loss of visual field is usually only realized on advanced glaucoma damage. However, glaucomatous progression can be significantly slowed or even halted if detected early enough [6]. This motivates the need for mass screening efforts to detect glaucoma at an early stage. However, currently, glaucoma screening is labor intensive as it requires manual grading of the retinal image by experienced professionals. This process is time-consuming and the need for a trained clinician raises the difficulty of conducting mass screening events. Furthermore, it has been reported that the accuracy in the assessment of glaucoma is subject to the experience and training of the observer [7]. Due to the limitations of the current manual method, there is hence a need for the development of an objective and computerized screening system for glaucoma screening.

Figure 1:
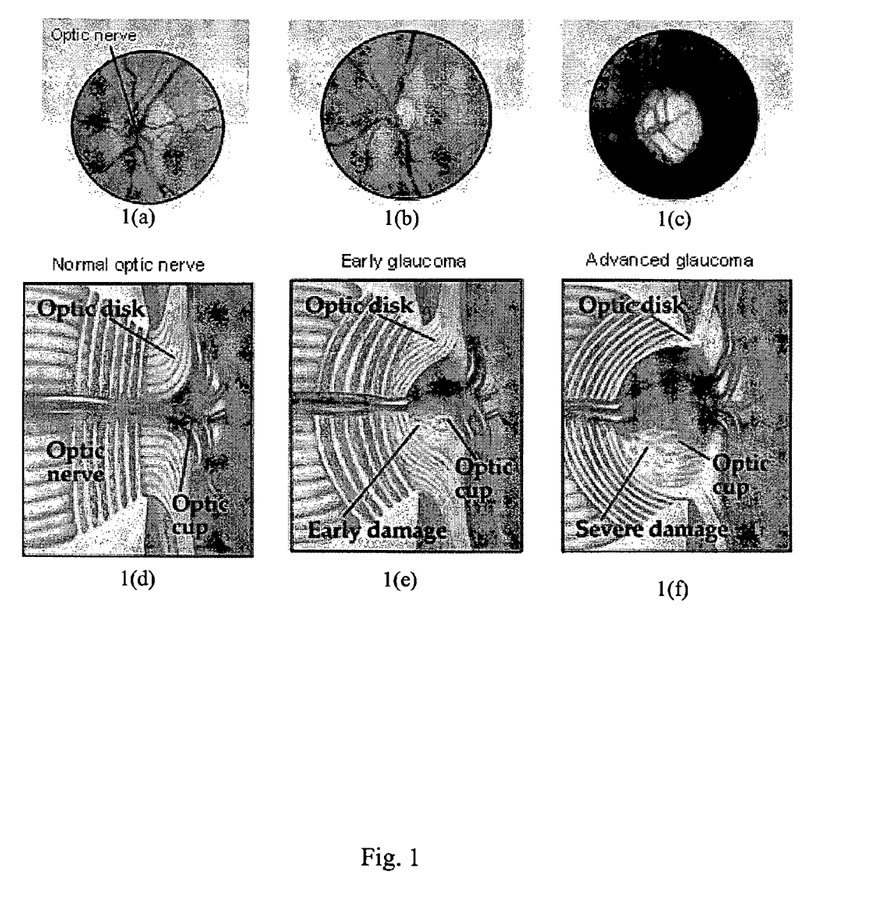
FIG. 1 is composed of FIGS. (a)-(f) which illustrate the physiology of the non-glaucomatous and glaucomatous retina.

FIG. 1(a) is a 2D retinal image of an eye which does not exhibit glaucoma, and FIG. 1(d) is a corresponding schematic diagram of the rear of the eye in partial cut-away view. The optic nerve transmits visual information from the eye to the brain and the optic nerve head, also known as the optic disc, is the start of the optic nerve in the retina. The optic disc is a structure by which the nerve fibers leave the retina. Within the optic disc is a depression known as the optic cup.

Glaucomatous optical neuropathy is physiologically characterized by an increased excavation of the optic cup, causing an increase in the size of the optic cup in relation to the optic disc. In FIGS. 1(b) and 1(e), which correspond in meaning respectively to FIGS. 1(a) and 1(d), the physiology of an eye with early glaucoma is illustrated, whereas in FIGS. 1(c) and 1(f), which again correspond in meaning respectively to FIGS. 1(a) and 1(d), the physiology of an eye with late glaucoma is shown. As shown in these figures, there is a loss of ganglion cells and a thinning of the nerve fibers when glaucoma is present. In addition, there is also an increased excavation of the optic cups in the glaucomatous eyes.

A standard feature employed by current methods for the risk assessment of glaucoma in a patient is the measurement of the ratio between the optic cup and the optic disc, more commonly known as the cup to disc ratio (CDR). The CDR is used to provide a quantitative measure of the relative cup to disc size. Typically, if the CDR is high, this represents a higher risk of glaucoma and further examination may be recommended.

To obtain the CDR, it is necessary to isolate the optic disc and the optic cup from each other and from the rest of the retinal image. Previously, many methods have been reported for optic disc detection, but significantly fewer methods have been presented for optic cup detection. Optic cup detection is much more challenging due to the reduced visibility of the optic cup within the optic disc and the high density of vascular architecture traversing the optic cup boundary. One of the earliest reported methods for optic cup detection was based on the discriminatory analysis of color intensity [8]. Further methods for optic cup detection were subsequently developed. For example, pixels within the retinal image were classified based on pixel features generated from stereo color retinal images [9]. Gradient, shape and depth parameters obtained from prior stereoscopic reconstruction were used to derive the energy function for the cup in [10] and a variational level set method based on pixel intensity was used to globally optimize the obtained cup contour in [11].

The pixel color intensity, or pallor, and the associated gradients form the basis of the previously described methods for cup segmentation. When cup pallor is used to determine the size of the cup, there is a potential risk of understating the cup size. This results in an effect known as pallor/cup discrepancy, where the area of pallor lags behind the actual cup size [12]. In addition, when the difference in pallor between the cup and the disc is not particularly visible, especially in early glaucomatous atrophy when the cup can be shallow, the accurate determination of the cup size using pallor alone can be challenging. In addition, many of the methods [9, 10] further depend on the processing of stereoscopic images to obtain the cup boundary.

There is hence a need for a method and system for determining an optic cup boundary which can overcome the above problems.

SUMMARY OF THE INVENTION

The present invention aims to provide new and useful computerized systems for identifying the optic cup.

In general terms, the present invention proposes that kinks in blood vessels approximately at the boundary between the optic cup and the optic disc are used to identify the edges of the optic cup. Certain embodiments of the invention thus make possible a computerized system to identify the optic cup in 2D retinal images which does not rely on colour differences as in prior art systems.

It is not entirely unknown to use kinks in blood vessels as an aid to observing an optic cup as this is mentioned very briefly in [13]. However, it is challenging to use such a method due to the difficulty in detecting the small vessels in the optic disc. Furthermore, the disclosure in [13] was in the context of manual inspection of stereoscopic images, and there is no disclosure that such a technique is of use (or even possible) in 2D images. There is no suggestion that it would be possible to perform the technique without human intervention. Nor is there any suggestion that this can be done by a procedure comprising a computerized identification of the edges of blood vessels.

Specifically, a first aspect of the present invention is a method for determining an optic cup boundary in a 2D retinal image, the method comprising the steps of: (a) making a preliminary estimate of the position of the optic cup boundary on the image; (b) identifying the edges of blood vessels in a neighborhood of the preliminary estimate of the position of the optic cup boundary; (c) detecting kinks in the identified blood vessel edges; and (d) determining the optic cup boundary in the 2D retinal image based on the detected kinks.

The "neighborhood" here may be the sum of a plurality of patches defined overlapping with the preliminary estimate of the position of the optic cup boundary.

The invention may alternatively be expressed as a computer system for performing such a method. This computer system may be integrated with a device for capturing 2D retinal fundus images. The invention may also be expressed as a computer program product, such as one recorded on a tangible computer medium, containing program instructions operable by a computer system to perform the steps of the method.

BRIEF DESCRIPTION OF THE FIGURES

An embodiment of the invention will now be illustrated for the sake of example only with reference to the following drawings, in which:

FIG. 3 (a)-(c) illustrate the original image and the results of steps 202-204 of FIG. 2;

FIG. 4 (a)-(d) illustrate the results of steps 206-216 of FIG. 2;

DETAILED DESCRIPTION OF THE EMBODIMENTS

Figure 2:
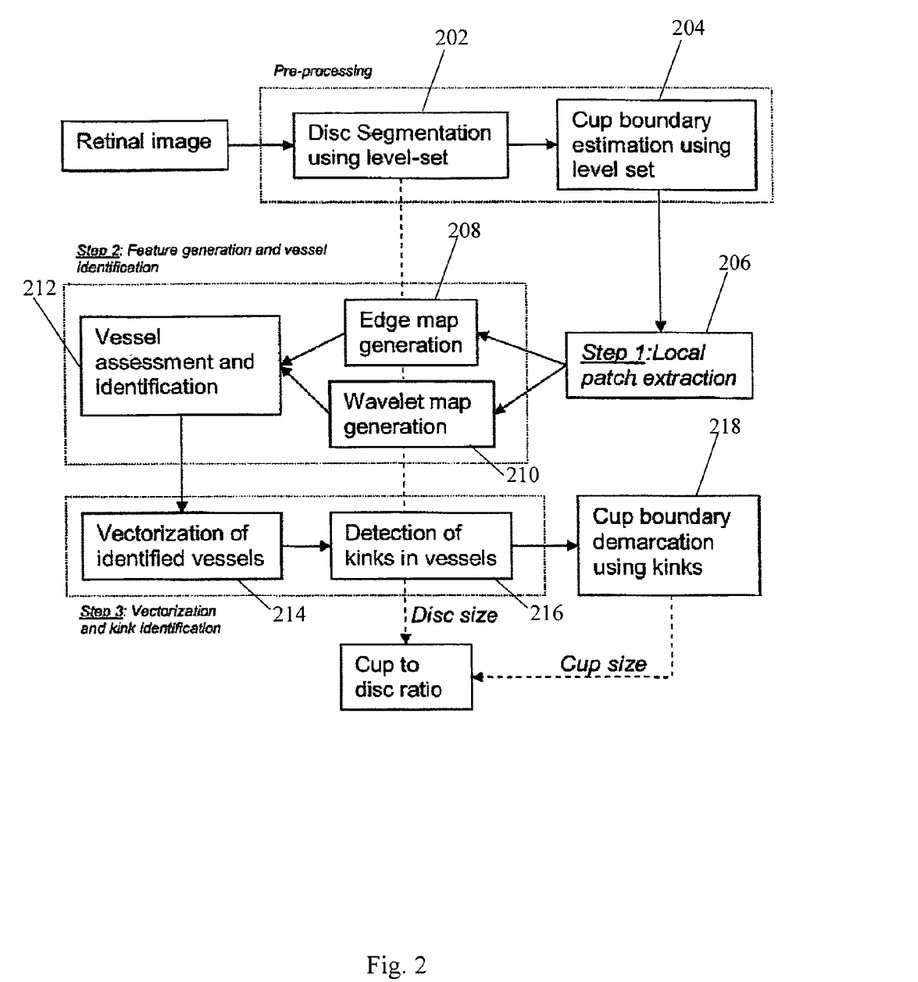
FIG. 2 illustrates a flow diagram of a method of determining optic cup boundary in an embodiment of the present invention.

Referring to FIG. 2, the steps are illustrated of a method which is an embodiment of the present invention, and which determines the cup to disc ratio for the assessment of glaucoma using computerized kink detection.

The input to the embodiment is a single retinal image. Pre-processing involving steps 202 and 204 is first performed on the retinal image to obtain an estimate of the optic disc boundary on the image, and a preliminary estimate of the position of the cup boundary on the image. Next, local patch extraction (step 206) is performed on the preliminary estimate of the position of the cup boundary, the patches together defining a region proximate the preliminary estimate of the position of the cup boundary. This is followed by a process of "feature generation and vessel identification" involving steps 208, 210 (in which significant features on the patches are identified) and 212 (in which it is determined which of these features relate to blood vessel edges). The blood vessel edges are vectorized (step 214), and kinks are identified (step 216), after which cup boundary demarcation using kinks is performed in step 218 to obtain the cup size. This cup size is then compared with the output of step 202 to give the cup-to-disc ratio. These steps will now be described in more detail.

Pre-processing (Steps 202 and 204)

In step 202, disc segmentation is performed. In a retinal image, the optic disc occupies a small area of the entire retinal image. A region centered on the estimated disc location is first extracted. In one example, the diameter of the region is twice the typical optic disc diameter. The estimated disc centre is determined by thresholding the red channel of the retinal image where the disc is most apparent. Next, a variational level-set method [14] is applied to the region to obtain the optic disc. The obtained disc boundary is then smoothed using ellipse fitting.

In step 204, cup boundary estimation is performed. Thresholding is applied to the green channel of the extracted optic disc to obtain an initial contour for the subsequent application of the variational level-set method. The results obtained after applying the variational level-set method are then ellipse-fitted to provide a preliminary estimate of the position of the cup boundary based on pallor.

Local Patch Extraction (Step 206)

In step 206, local patch extraction is performed, to localize the kinks lying within the optic disc. A plurality of square patches are generated using a preliminary estimate of the position of the cup boundary as a guide. In example embodiments, the spacing between the patches is designed in such a way so as to ensure that there is some overlap between the patches to provide a measure of redundancy. Furthermore, in example embodiments, the size of the square patches is 128× 128 pixels, and there are sufficient patches that collectively the set of patches includes the whole of the preliminary estimate of the position of the cup boundary. By employing localized patches of interest, the skewing of the subsequent edge detection method towards detecting only the large vessels can be avoided.

Figure 3:
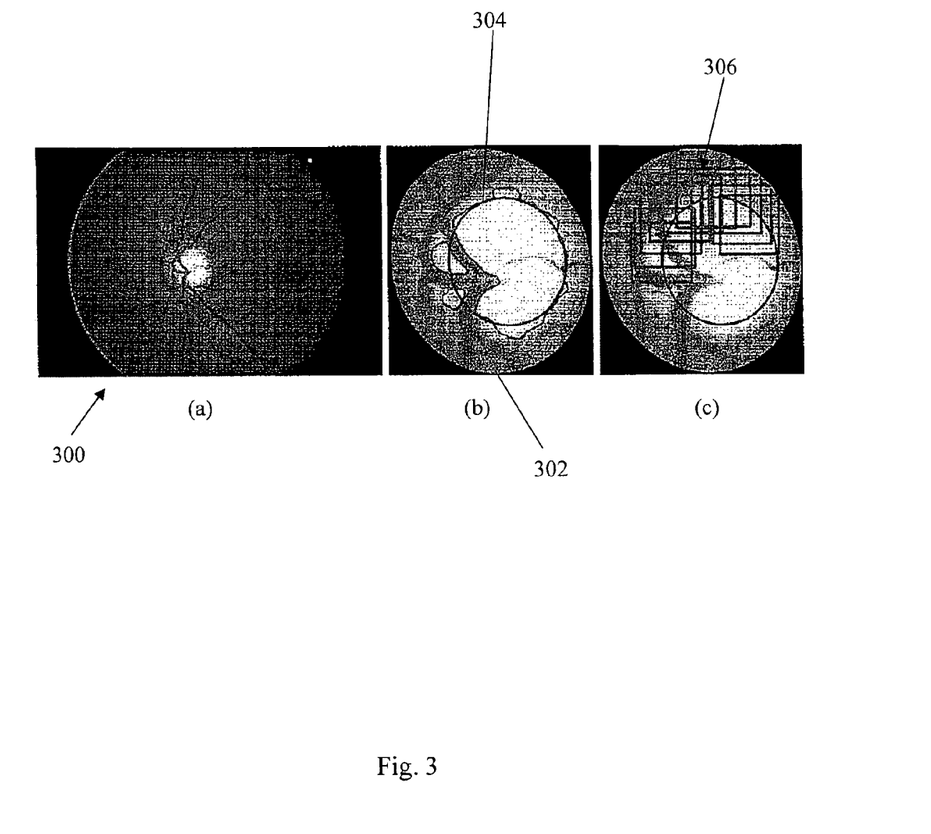

FIG. 3(a) illustrates an initial retinal image 300, whereas FIG. 3(b) illustrates the extracted optic disc boundary 302 and preliminary estimate of the optic cup boundary 304 after steps 202 and 204 are performed. Some of the generated patches 306 after performing step 206 are shown in FIG. 3(c). In reality, the number of patches is sufficient to together cover the whole of the line 304.

Feature Generation Including Steps 208, 210 and 212

One of the key challenges in the detection of kinks lies in the extraction of small vessels due to their reduced visibility compared to larger vessels. To detect kinks, it is more important to detect bending of the vessels rather than the vessels themselves. Therefore, the required kink information can also be obtained from vessel edges. In the embodiments of the present invention, the embodiment detects kinks by detecting intra-disc vessel edges using two independent approaches to generate features.

In step 208, edge map generation is performed on each of the patches extracted in step 206. Edge detection is applied in the green channel of the patches to obtain the location of all possible vessel edges within the patches. In one example, the canny edge transform is used. However, other edge detection methods such as the Sobel, Prewitt or Roberts edge detection method can also be used. The resulting transform map G(x) is defined in Equation (1) where n is the detected edge number, $L_n$ refers to the nth detected edge and m is the total number of edges used $$G(x) = \begin{cases} 1 & \{x \mid x \in L_n, n = 1: m\} \\ 0 & \text{otherwise} \end{cases} \quad (1)$$

By performing edge detection on localized patches, the dominance of larger vessels (with corresponding higher contrasts at the vessel edges) is reduced. This allows the detection of smaller vessels with lower vessel edge contrasts. Small vessel visibility may be subsequently improved via image contrast enhancement. However, if applying the image contrast enhancement results in increased noise effects which may in turn result in the detection of superfluous edges, it is preferable not to apply the image contrast enhancement.

In step 210, wavelet map generation is performed on each of the patches extracted in step 206 by applying wavelet transform to the green channel of each patch. In one example, a 2D continuous wavelet transform as shown in Equation (2) is used. In Equation (2), $W_\psi$ is the wavelet response whereas x=(x,y) is the pixel value; $C_\psi$, $\psi$, b, $\theta$, and s denote the normalizing constant, the mother wavelet, the displacement vector, the rotation angle and the dilation parameter respectively. $\psi^*$ is the complex conjugate of $\psi$. The 2D Gabor Wavelet Transform $\psi_G(x)$ as shown in Equation (3) is used as the mother wavelet, where A=diag[$\epsilon^{-1/2}$, 1], $\epsilon$>=1 is a 2×2 diagonal matrix that defines the anisotropy of the filter, and $k_0$ is a vector that defines the frequency of the complex exponential.

$$W_\psi(b, \theta, s) = C_\psi^{-1/2} \frac{1}{s} \int \psi^*(s^{-1} r_{-\theta}(x-b)) f(x) d^2 x \quad (2)$$

$$\psi_G(x) = \exp(j k_0 x) \exp\left(-\frac{1}{2} \|Ax\|^2\right) \quad (3)$$

In the wavelet transform, sections of the image which have a high correlation to the mother wavelet generate a higher score or value. The image is analysed for these maximum values of the wavelet response, which are then used to produce a wavelet transform map. The results from the wavelet transform i.e. the wavelet response characterize the probability (i.e. confidence) of the existence of vessels within the patch. This confidence is represented by the strength of the wavelet response which is in turn reflected by the intensity of the pixels in the wavelet transform map.

Normalization of the wavelet map may be performed according to Equation (4). In Equation (4), W(x) and $W_{norm}$(X) represents the wavelet map and the normalized wavelet map respectively, $\mu_W$ represents the mean of the wavelet coefficients in the wavelet map and $\sigma_W$ represents the standard deviation of the wavelet coefficients in the wavelet map.

$$W_{norm}(x) = \frac{W(x) - \mu_W}{\sigma_W} \quad (4)$$

In step 212, vessel assessment and identification is performed. The outputs of steps 208 and 210 i.e. the edge map and the wavelet transform map, are statistically combined to obtain a confidence map whereby each pixel in the confidence map indicates the probability that the pixel belongs to a vessel edge. In one example, a Bayesian rule is used for the combination. Following this, the overall probability of each group of pixels being an actual vessel edge is determined by averaging the pixel probabilities within the group of pixels.

In one example, the generation of the confidence map and the averaging of the pixel probabilities within the group of pixels are performed according to Equation (5). In Equation (5), $\delta_n$ represents the confidence map for a group of pixels after the combination of the normalized wavelet map, $W_{norm}$($x_{n_p}$) and the edge map, $G(x_{n_p})$ and after the averaging of the pixel probabilities within the group of pixels where $N_p$ is the number of pixels in the group.

$$\delta_n = \frac{\sum_{n_p=1}^{N_p} W_{norm}(x_{n_p}) \times G(x_{n_p})}{N_p} \quad (5)$$

An empirically optimized cutoff is then used to remove pixel groups with a low average probability. In this way, the group of pixels whose pixels correspond to low probability values are treated as superfluous and are filtered out. This leaves only high-probability groups of pixels which are most likely to be vessel edges i.e. the high-probability groups of pixels are the detected edges.

Alternatively, adaptive methods such as Bayesian or Support Vector Machines can be used to select vessel edges. A training period may be required in these methods and the training data used may be the clinical data obtained from the Singapore Eye Research Institute as elaborated further below.

Vectorization and Kink Detection (Steps 214 and 216)

In step 214, vectorization of the identified vessels is performed. The presence of one- or two-pixel protrusions, rather than actual kinks, along some of the detected vessel edges may be observed due to the presence of noise in the image. To avoid these effects, each vessel edge is smoothed by the application of a polynomial of order n, where n is allowed to vary to obtain the best fit. To avoid over-fitting, the maximum order, n, of the polynomial is limited (n may range from 5 to 15, depending on the requirements of the user). Following this, each vessel edge is subdivided into line segments, which are then vectorized. This helps in avoiding further local effects.

In step 216, detection of kinks in the vessels is performed. The change in the relative angle between each node in each vessel is calculated and a kink is identified as being present at a node if the change in angle is found to be more than a specified angle, which can range from 15 degrees and above and can be modified to suit the sensitivity requirements of the user. In vessels where the change in angle is similar at several successive nodes, a kink is not identified as being present even at where the relative angle at each node exceeded the specified angle as this scenario typically indicates a curving vessel rather than a localized kink.

Figure 4:
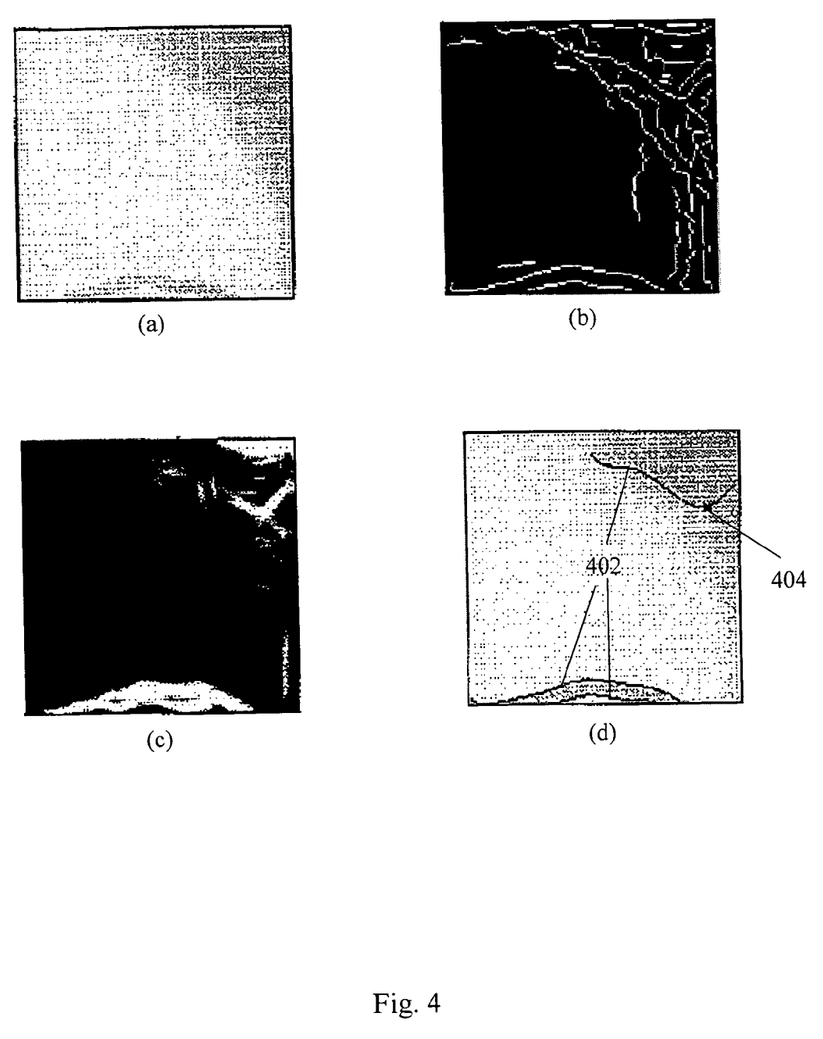

FIG. 4 illustrates the retinal images after performing steps 206-216. FIG. 4(a) illustrates an extracted patch from step 206. FIG. 4(b) illustrates the edge map after step 208 is applied on the green channel of the extracted patch. FIG. 4(c) illustrates the wavelet map after step 210 is applied on the green channel of the extracted patch. FIG. 4(d) illustrates the image in FIG. 4(a) with superimposed detected vessel edges 402 (lines) and kink 404 (cross) after steps 212-216 are applied.

Cup Boundary Demarcation Using Kinks (Step 218)

After processing all the patches according to steps 214 and 216, the detected vessels and the identified kinks are extracted from the patches and are registered with the region which is within the estimate of optic disc obtained in step 202. The various identified vessels from different patches are merged whereas kinks from different patches but which are in close pixel proximity with each other are combined.

Figure 5:
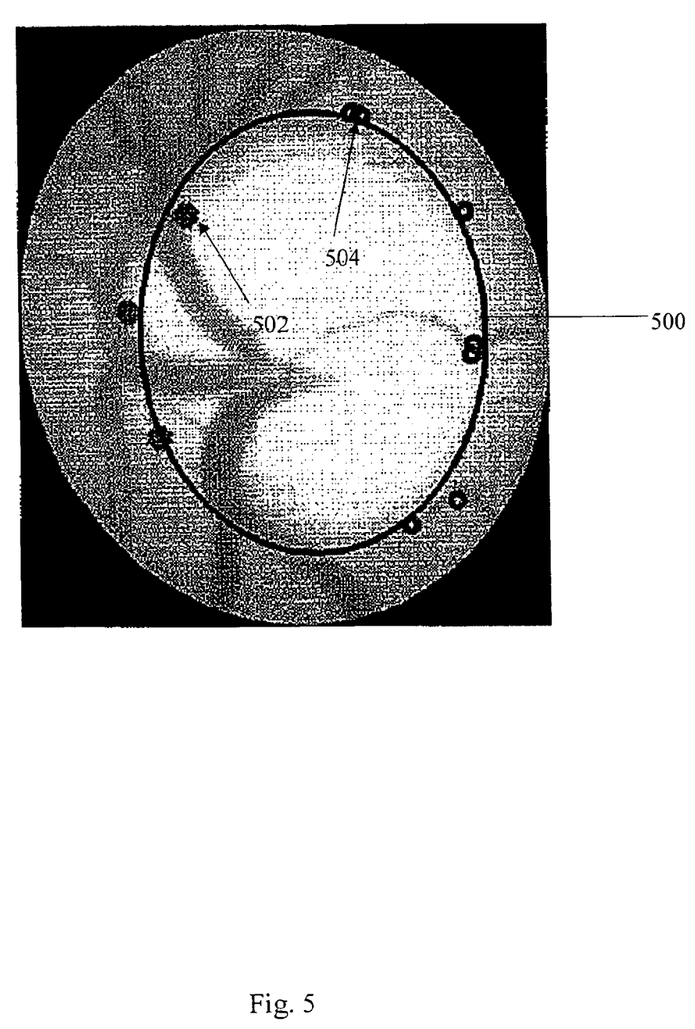
FIG. 5 illustrates the result of the process of FIG. 2.

The cup boundary is then estimated using the kinks. When more than one kink is detected in a combined vessel, which is possible in severe kinking or 'bayoneting', the kink furthest from the optic disc centre is used to indicate the location of the cup boundary. Ideally, for an estimation of the cup boundary using kinks only, the kinks should be well-distributed around the cup boundary. However, this is not always the case. In some images, the kinks may be clustered in a particular region, or there may be insufficient kinks to identify the overall cup boundary. In such cases, additional points from the pallor-based level-set cup boundary obtained from the step 204 (see FIG. 2) are automatically added. Finally, the cup boundary is obtained via ellipse fitting the kinks and any additional points. FIG. 5 illustrates an example of the cup boundary 500 found using a combination of kink points 502 and pallor points 504.

Experimental Results 27 retinal images were obtained from the Singapore National Eye Centre (SNEC) for the experiment. Each retinal image was captured using a high-resolution 3072×2048 retinal fundus camera, and was subsequently graded by clinician-scientists from SNEC to determine the cup to disc ratio ($CDR_{gt}$). The results from the grading are set as the ground truth upon which the performance of the embodiment is evaluated. The image set was then divided into two groups, with one group consisting of 10 images taken from glaucomatous subjects, and another group consisting of the remaining 17 images from non-glaucomatous subjects. The diagnosis of glaucoma was based on an overall approach which incorporated CDR values, intraocular pressure and visual field defect tests.

Using these 27 images, the accuracy of the kink-based method (KBM) used by the embodiment in the determination of the CDR (i.e. kink-based CDR value) was evaluated by calculating the difference ($E_{KBM}$) between the kink-based CDR value ($CDR_{KBM}$) and the clinical CDR ($CDR_{gt}$) i.e. $E_{KBM}=CDR_{gt}-CDR_{KBM}$. As a means of comparison, the CDR was obtained using the pallor-only method (PBM) and the error $E_{PBM}$ was similarly calculated by calculating the difference $E_{PBM}$ between the pallor-only CDR value ($CDR_{PBM}$) and the clinical CDR ($CDR_{gt}$) i.e. $E_{PBM}=CDR_{gt}-CDR_{PBM}$.

Figure 6:
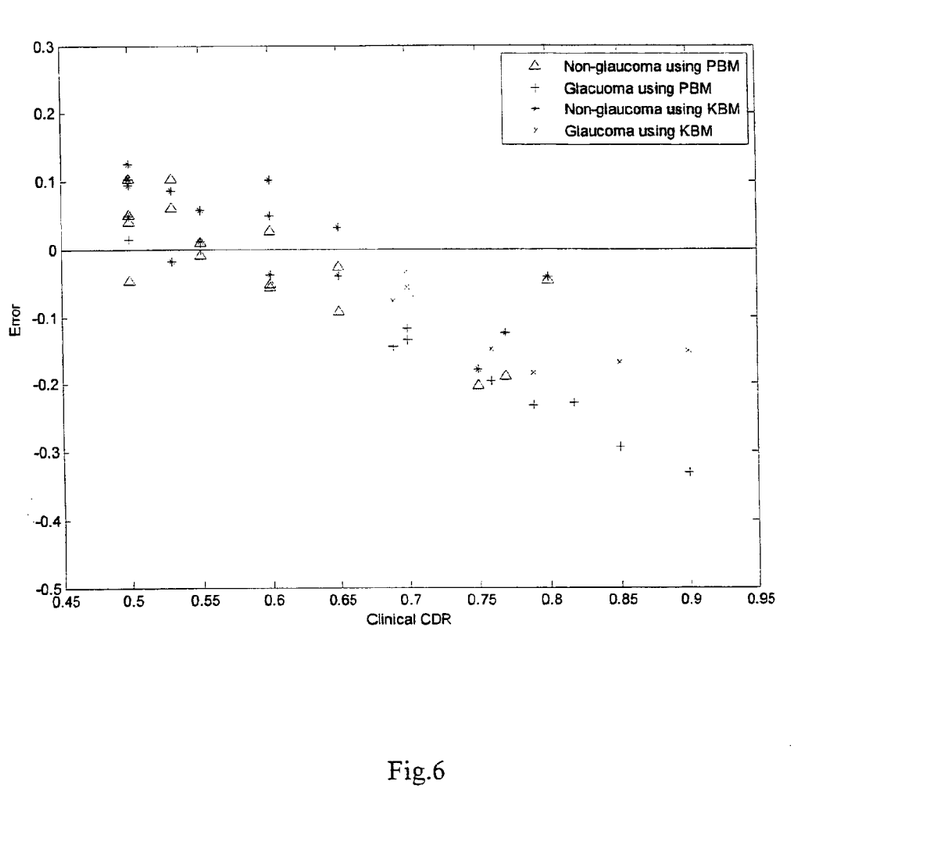
FIG. 6 illustrates a plot of the errors obtained from the process of FIG. 2 and from a prior art method.

FIG. 6 illustrates a plot of $E_{KBM}$ and $E_{PBM}$ against $CDR_{gt}$. It can be seen from FIG. 6 that for both glaucomatous and non-glaucomatous subjects, the errors were lower at higher CDR values. In particular, at higher CDR values (where the risk of contracting glaucoma is higher), the errors were nearly halved. To determine the average error difference between the kink-based method and the pallor-only method, RMS errors were calculated using the $E_{KBM}$ and $E_{PBM}$ values. The RMS errors calculated from the $E_{KBM}$ and $E_{PBM}$ values were found to be 0.093 and 0.139 respectively, indicating a reduction in error of 33% when the kink-based method was used. Furthermore, it was also observed that the range of error for $E_{KBM}$ is within 0.2 CDR units, which is within previously reported manual intra-observer limits [7]. Although the CDR alone is insufficient to determine if a patient has glaucoma, the CDR can be used in early screening systems as a convenient and objective means of indicating if a patient has a high risk of contracting glaucoma.

Based on recommendations from SNEC, a CDR value of more than 0.6 CDR units indicates a risk of contracting glaucoma. Therefore, the image set was classified into "high risk" if CDR is more than 0.60, and "low risk" otherwise. The specificity and sensitivity of the kink-based method and the pallor-only based method in classifying the retinal images into the "high risk" category (i.e. CDR>0.6) were calculated and are shown in Table 1. The results indicate a much higher sensitivity for the kink-based method. Although the kink-based method has a lower specificity as compared to the pallor-only based method, the kink-based method is still preferable in screening systems as the tolerance level for false positives is generally higher than that for false negatives in screening systems.

TABLE 1

| Method | RMS error | Sensitivity (CDR >0.6) | Specificity (CDR >0.6) |
|---|---|---|---|
| Pallor-only based method | 0.139 | 0.186 | 0.818 |
| Kink-based method | 0.093 | 0.813 | 0.455 |

Figure 7:
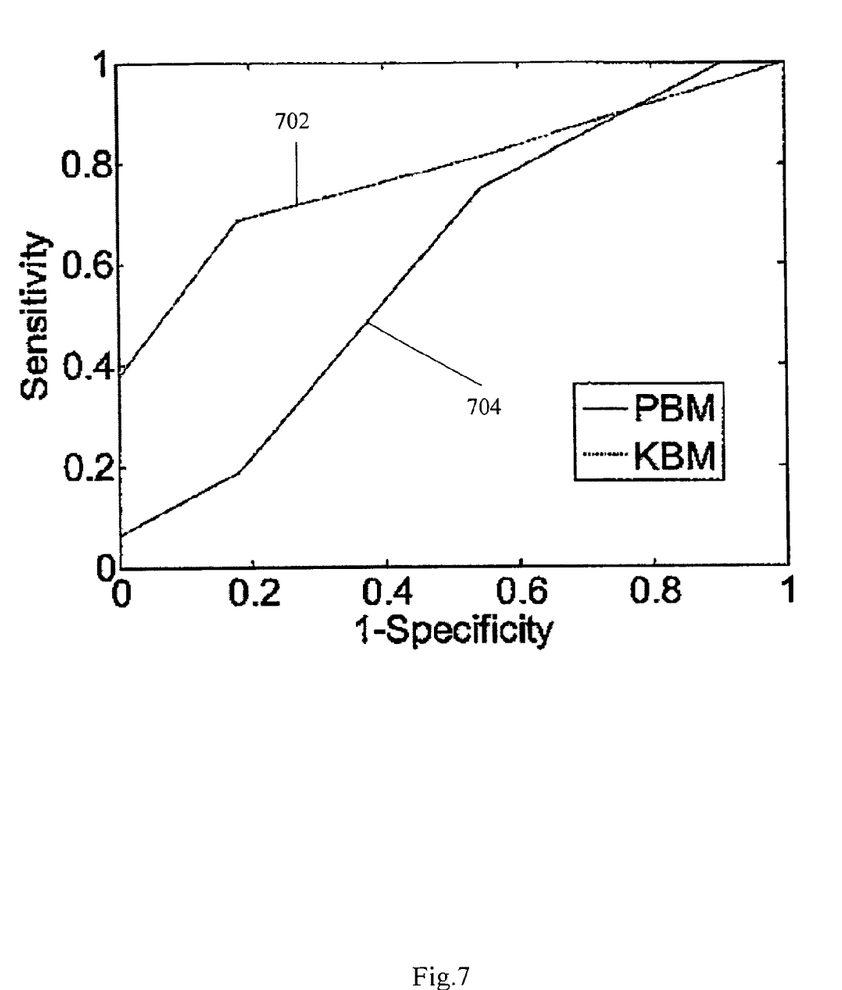
FIG. 7 illustrates ROC curves constructed from the results of the process of FIG. 2 and from a prior art method.

FIG. 7 illustrates the Receiver Operating Characteristics (ROC) curves constructed using the results from the kink-based method (curve 702) and the pallor-only based method (curve 704) to further evaluate the performance of these methods in classifying images into the "high risk" category based on the CDR. To obtain the ROC curves, the CDR cutoff value for indicating that an image belongs to the "high risk" category was varied even though the clinical ground truth CDR cutoff value for indicating a high risk of glaucoma was maintained at 0.6 CDR units. From the results, it can be seen that the kink-based method in general performs better than pallor-only based method.

The embodiment using the kink-based method has the advantage that it allows an automated determination of CDR from retinal images, thus allowing an automated assessment of the risk of contracting glaucoma in a patient. By the word "automated", it is meant that once initiated by a user, the entire process in the present embodiment is run without human intervention. Alternatively, the embodiments may be performed in a semi-automated manner, that is, with minimal human intervention. The embodiment using the kink-based method is also more consistent and less labour intensive than manual grading of the retinal images. This can facilitate mass screenings and allow early detection of glaucoma in patients.

Furthermore, unlike other methods, the embodiment does not rely on 3D modalities such as stereoscopic images. Rather, the embodiment simply requires a single 2D retinal image. This enables increased functionality on lower-cost equipment.

By not relying on colour information from the retinal images, the embodiment can operate even in the absence of pallor or visible disc-cup contrast. The embodiment is also resilient to problems such as the cup/pallor discrepancy. Therefore, the kink-based method in the embodiment is more accurate than other methods, such as the pallor-only based method and provides a physiologically and medically sound approach for cup boundary determination.

The embodiment can be used in screening centres for the computerized evaluation of the CDR without the need for an experienced grader. Some of the present inventors have previously proposed a system called the "ARGALI system" (as disclosed in PCT/SG2008/000186, which was unpublished as at the priority date of the present application, but the disclosure of which is hereby incorporated by reference).

Briefly, the ARGALI system disclosed that a single 2D retinal fundus image is processed by a step of optic disc segmentation followed by a step of cup segmentation. Data derived from the optic disc segmentation step (i.e. the output of the disc segmentation step and/or data derived from the output of the optic disc segmentation step, e.g. by a smoothing operation) and data derived from the output of the optic cup segmentation step (i.e. the output of the cup segmentation step and/or data derived from the output of the optic disc segmentation step, e.g. by a smoothing operation) are fed to an adaptive model which has been trained to generate from such inputs a value indicative of CDR. The ARGALI technique may be combined with the present embodiment to provide a more comprehensive and holistic approach for CDR determination. For example, by obtaining useful information regarding the cup boundary based on kinks, the present embodiment employing such structural information may complement the ARGALI system such that the results from the original ARGALI system obtained using the colour of the optic cup can be adjusted with the cup boundary markers derived from the present embodiment to obtain more accurate results.

A comparison between our system and three prior art systems is summarized in Table 2.

TABLE 2

|  | Technology of cup detection | Reliance on pixel colours | Cup-pallor discrepancy | Limitation |
| --- | --- | --- | --- | --- |
| Prior Art [8] | Discriminatory analysis-based Thresholding | Yes | Yes | Colour information may be inaccurate |
| Prior Art [9] | Modified deformable model technique | Yes | Possible | Requires pre-processing of stereo retinal images to obtain cup information |
| Prior Art [10] | Pixel feature classification | Yes | Yes | Relies on features from stereo colour retinal images |
| Embodiments | Computerized kink identification as cup boundary marker | No | Less likely | |

REFERENCES

[1] World Health Organization, Magnitude and Causes of Visual Impairment, 2004
[2] T. Y. Wong, S. C. Loon, S. M. Saw, "The Epidemiology of Age Related Eye Diseases in Asia," *Br. J. Ophthalmol.*, Vol. 90, pp. 506-511, 2006.
[3] P. J. Foster, F. T. S. Oen, D. Machin, T.-P. Ng, J. G. Devereux, G. J. Johnson, P. T. Khaw and S. K. L. Seah, "The Prevalence of Glaucoma in Chinese Residents of Singapore: A Cross-Sectional Population Survey of the Tanjong Pagar District," *Arch Ophthalmol*, Vol. 118, pp. 1105-1111, 2000
[4] H. A. Quigley and A. T. Broman, "The number of people with glaucoma worldwide in 2010 and 2020," *Br J Ophthalmol*, Vol. 90, pp. 262-267, 2006
[5] Glaucoma Research Foundation, "Are You at Risk for Glaucoma?"
[6] A. Heijl, M. C. Leske, B. Bengtsson, L. Hyman, B. Bengtsson, M. Hussein, and G. for the Early Manifest Glaucoma Trial, "Reduction of Intraocular Pressure and Glaucoma Progression: Results From the Early Manifest Glaucoma Trial," *Arch Ophthalmol*, Vol. 120, pp. 1268-1279, 2002
[7] R. Ritch, M. B. Shields, T. Krupin, *The Glaucomas*, $2^{nd}$ ed., St. Louis: Mosby; 1996, pp 623
[8] N. Inoue, K. Yanashima, K. Magatani, and T. A. K. T. Kurihara, "Development of a simple diagnostic method for the glaucoma using ocular Fundus pictures," $27^{th}$ *Annual International Conference of the Engineering in Medicine and Biology Society*, 2005
[9] M. D. Abramoff, W. L. M. Alward, E. C. Greenlee, L. Shuba, C. Y. Kim, J. H. Fingert and Y. H. Kwon, "Automated Segmentation of the Optic Disc from Stereo Color Photographs Using Physiologically Plausible Features," *Investigative Ophthalmology and Visual Science*, Vol. 48, pp. 1665, 2007
[10] J. Xu, O. Chutatape, E. Sung, C. Zheng, and P. Chew Tec Kuan, "Optic disk feature extraction via modified deformable model technique for glaucoma analysis," *Pattern Recognition*, Vol. 40, pp. 2063-2076, 2007
[11] J. Liu, J. H. Um, D. W. K. Wong, X. Jia, F. Yin, H. Li and T. Y. Wong, "Image-Based Automatic Glaucoma Diagnosis." In *Asian Conference on Computer Aided Surgery Singapore*, 2007
[12] R. R. Allingham, K. F. Damji, S. Freedman, S. E. Moroi, and G. Shafranov, *Shields' Textbook of Glaucoma, $5^{th}$ Edition*: Lippincott Williams & Wilkins, 2005, pp. 88
[13] J. B. Jonas, W. M. Budde, and S. Panda-Jonas, "Ophthalmoscopic evaluation of the optic nerve head," *Surv Ophthalmol*, Vol. 43, pp. 293-320, 1999
[14] C. Li, C. Xu, C. Gui and M. D. Fox, "Level set evolution without re-initialization: a new variational formulation." *IEEE Computer Society Conference on Computer Vision and Pattern Recognition*, 2005

What is claimed is:

1. A method for determining an optic cup boundary in a 2D retinal image, the method comprising operations of:
    (a) making a preliminary estimate of the position of the optic cup boundary on the image;
    (b) identifying the edges of blood vessels in a neighborhood of the preliminary estimate of the position of the optic cup boundary;
    (c) detecting kinks in the identified blood vessel edges; and
    (d) determining the optic cup boundary in the 2D retinal image based on the detected kinks;
    (e) wherein operation (b) comprises:
        (i) generating patches proximate the preliminary estimate of the position of the optic cup boundary; and
        (ii) identifying blood vessel edges in each generated patch.

2. A method according to claim 1, wherein the generated patches overlap with each other.

3. A method according to claim 1 in which operation (c) comprises:
    (i) denoting each identified vessel edge in each generated patch as a series of nodes connected by vectors;
    (ii) calculating the angular differences between the extension direction of successive ones of the vectors; and
    (iii) determining that a kink is present if the calculated angular difference is larger than a specified threshold.

4. A method according to claim 3, wherein denoting the identified vessel edges as a series of nodes connected by vectors comprises:
    (i) fitting each identified vessel edge to a polynomial of order n to smooth each identified vessel edge, where n is an integer; and (ii) subdividing each smoothed vessel edge into line segments, each of said line segments corresponding to a respective one of said vectors.

5. A method according to claim 1, wherein identifying vessel edges in each generated patch further comprises:
   (a) performing edge detection on each generated patch to generate an edge map;
   (b) performing wavelet transform on each generated patch to generate a wavelet transform map;
   (c) combining the edge map and the wavelet transform map to generate a confidence map for each generated patch wherein each pixel in the confidence map indicates a probability that the pixel belongs to a vessel edge; and
   (d) identifying vessel edges by identifying pixels in the confidence map having a relatively high probability of corresponding to vessel edges.

6. A method according to claim 5, wherein the edge detection is performed using Canny edge detection, Sobel edge detection, Prewitt edge detection or Roberts edge detection.

7. A method according to claim 5, wherein the wavelet transform is performed using a 2D Gabor Wavelet Transform.

8. A method according to claim 5, wherein the edge map and the wavelet transform map are combined using a Bayesian rule or Support Vector Machine classification.

9. A method according to claim 5, wherein the wavelet transform map is normalized prior to combining the edge map and the wavelet transform map.

10. A method according to claim 1 in which operation (a) is performed by:
    (i) obtaining an estimate of the position of an optic disc boundary on the image; and
    (ii) obtaining said preliminary estimate of the position of the cup boundary from the estimate of the optic disc boundary.

11. A method according to claim 10 in which obtaining an estimate of the position of an optic disc boundary is performed by:
    (i) thresholding a red channel of the retinal image;
    (ii) determining a centre of the optic disc based on the thresholding of the red channel of the retinal image;
    (iii) extracting an optic disc region centered at the centre of the optic disc;
    (iv) applying a variational level-set method to the extracted optic disc region to obtain an initial estimate of the optic disc boundary; and
    (v) smoothing the initial estimate of optic disc boundary using ellipse fitting to obtain the estimate of optic disc boundary.

12. A method according to claim 11, wherein the diameter of the optic disc region is at least 1.5 times the diameter of a typical optic disc.

13. A method according to claim 11, wherein obtaining said preliminary estimate of the position of the cup boundary from the estimate of the optic disc boundary comprises:
    (i) thresholding a green channel of the region within the estimate of the optic disc boundary to obtain a first contour;
    (ii) applying a variational level-set method to the first contour to obtain a second contour; and
    (iii) applying ellipse fitting to the second contour to obtain the preliminary estimate of the position of the optic cup boundary.

14. A method according to claim 1 in which operation (d) comprises performing an ellipse fitting algorithm to the detected kinks.

15. A method according to claims 1, wherein operation (d) comprises:
    (i) identifying points on the preliminary estimate of the position of the optic cup boundary; and
    (ii) performing an ellipse fitting algorithm on the detected kinks and said identified points.

16. A method according to claim 1, further comprising:
    determining a disc size from the optic disc boundary;
    determining cup size from the optic cup boundary; and
    determining a CDR by calculating the ratio of the cup size to the disc size.

17. A method according to claim 16 further comprising determining that a risk of contacting glaucomatous is high if the CDR is greater than 0.6.

18. A computer system having a processor and a data storage device, the data storage storing instructions operable by the processor to cause the processor to determine an optic cup boundary in a 2D retinal image by performing the operations of:
    (a) making a preliminary estimate of the position of the optic cup boundary on the image;
    (b) identifying the edges of blood vessels in a neighborhood of the preliminary estimate of the position of the optic cup boundary;
    (c) detecting kinks in the identified blood vessel edges; and determining the optic cup boundary in the 2D retinal image based on the detected kinks;
    (d) wherein operation (b) comprises:
        (i) generating patches proximate the preliminary estimate of the position of the optic cup boundary; and
        (ii) identifying blood vessel edges in each generated patch.

19. A non-transitory computer program product, readable by a computer system and containing instructions operable by a processor of the computer system to cause the processor to determine an optic cup boundary in a 2D retinal image by performing the operations of:
    (a) making a preliminary estimate of the position of the optic cup boundary on the image;
    (b) identifying the edges of blood vessels in a neighborhood of the preliminary estimate of the position of the optic cup boundary;
    (c) detecting kinks in the identified blood vessel edges; and
    (d) determining the optic cup boundary in the 2D retinal image based on detected kinks;
    (e) wherein operation (b) comprises:
        (i) generating patches proximate the preliminary estimate of the position of the optic cup boundary; and
        (ii) identifying blood vessel edges in each generated patch.

* * * * *